United States Patent [19]
Landis

[11] Patent Number: 5,881,745
[45] Date of Patent: Mar. 16, 1999

[54] FINGER FLOSSER

[75] Inventor: Timothy J. Landis, Loomis, Calif.

[73] Assignee: OP-D-OP, Inc., Roseville, Calif.

[21] Appl. No.: 122,175

[22] Filed: Jul. 24, 1998

[51] Int. Cl.$^6$ .................................................. A61C 15/00
[52] U.S. Cl. .......................................... 132/323; 132/325
[58] Field of Search .................................... 132/321, 323, 132/324, 325, 326, 327, 328, 329; 600/104; 606/113, 137

[56] References Cited

U.S. PATENT DOCUMENTS

| | | |
|---|---|---|
| 4,016,892 | 4/1977 | Chodorow . |
| 4,206,774 | 6/1980 | Griparis . |
| 4,802,752 | 2/1989 | Chodorow . |
| 5,503,168 | 4/1996 | Wang . |

*Primary Examiner*—Gene Mancene
*Assistant Examiner*—Philogene Pedro
*Attorney, Agent, or Firm*—John P. O'Banion

[57] ABSTRACT

A dental floss apparatus generally comprising a thimble, a pair of tines extending from the top surface of the thimble and a section of dental floss suspended between the tips of the tines. To floss, a forefinger or thumb is typically inserted into the thimble, which remains relatively fixed onto the forefinger or thumb by pressing the opposing forefinger or thumb on the same hand onto the side of the thimble. The thimble is sized and configured such that insertion of the forefinger or thumb causes a suction within the thimble that further aids holding the thimble. The section of dental floss across the tips is used to floss between the teeth. In an alternate configuration, a single tine extends upward from said thimble and dental floss is suspended between the tip of the tine and the thimble. In still another configuration, a second thimble is attached in tandem onto the first thimble for additional torque control. In lieu of the second thimble, a finger holder is attached in tandem onto the first thimble for torque control.

31 Claims, 11 Drawing Sheets

FIG. - 15

FINGER FLOSSER

CROSS-REFERENCE TO RELATED APPLICATIONS

Not Applicable

STATEMENT REGARDING FEDERALLY SPONSORED RESEARCH OR DEVELOPMENT

Not Applicable

REFERENCE TO A MICROFICHE APPENDIX

Not Applicable

BACKGROUND OF THE INVENTION

1. Field of the Invention

This application pertains generally to dental hygiene and more particularly to a one-piece disposable apparatus for teeth flossing.

2. Description of the Background Art

Dental flossing is an often unpleasant but necessary routine for good oral hygiene. The conventional method for flossing teeth involves grasping opposite ends of a length of dental floss with each hand, and manually manipulating the floss back and forth between the teeth. Anyone who has performed this arduous, but necessary, task is well aware that the nature of dental floss inherently makes it difficult to securely grasp and tautly hold a tensioned strand while maneuvering and manipulating the suspended section between all the teeth in an effort to floss. The smoothness of the floss, in addition to the saliva, prevents the fingers and hand from getting a secure grip, so the ends of the floss are usually wrapped around the fingers to maintain tautness. Those who have flossed in this conventional manner are aware that a tightly wrapped finger is uncomfortable, if not downright painful. Often the wrapped fingers turn purplish and begin to numb due to a lack of blood flow. Such inconveniences and difficulties spurred the development of various means to hold the dental floss while teeth flossing.

To alleviate such problems, means were developed to hold the dental floss while flossing. One such means is to provide short sections of approximately 4½ inches of floss having stub sections or gripper handles at both ends of the floss section. Dental floss having gripper handles is taught in U.S. Pat. No. 4,016,892, which is incorporated herein by reference.

Another known means developed to hold dental floss included a pair of sleeves fitted over the fingertips. One sleeve serves as the supply sleeve containing pre-wound floss, and the other sleeve serves as the take-up sleeve for receiving spent floss. To floss, both fingers are inserted into the mouth with the sleeves fitted thereon and the section of floss suspended between the sleeves is used to floss between teeth.

The problem common to both of the foregoing flossing devices is that at least two fingers must be inserted into the mouth, especially when flossing between the rear molars. This often proves to be unwieldy and cumbersome as the mouth must be opened widely to allow insertion of the fingers therein.

There are presently no known one-piece disposable dental flossers which can floss teeth using only one finger inserted into the mouth. Accordingly, there is a need for a low cost disposable dental flosser which is capable of one-finger dental flossing. The present invention satisfies this need, as well as others, and overcomes the deficiencies found in the prior art.

BRIEF SUMMARY OF THE INVENTION

The present invention is a dental floss apparatus generally comprising a thimble, a pair of tines extending from the top of the thimble and a section of dental floss suspended across the tips of the tines. To floss, a forefinger or thumb is typically inserted into the thimble, which remains relatively fixed onto the forefinger or thumb by pressing the opposing forefinger or thumb on the same hand onto the side of the thimble. The thimble is sized and configured such that insertion of the forefinger or thumb causes a suction within the thimble that further aids holding the thimble. The section of dental floss across the tips is used to floss between the teeth.

In an alternate configuration, a single tine extends from the top of the thimble and a section of dental floss is suspended from the tip of the tine to the thimble. In the alternate configuration, the effective flossing length of the floss if increased and this embodiment is particularly well suited to flossing rear molars. In still another configuration, a second thimble is attached in tandem onto the first thimble for additional torque control. In lieu of the second thimble, a finger holder is attached in tandem onto the first thimble for torque control.

An object of the invention is to provide a dental floss apparatus that eases dental flossing by relieving the discomfort of wrapping dental floss around the fingers.

Another object of the invention is to provide a single use disposable dental floss apparatus that is inexpensive and easy to manufacture.

Still another object of the invention is to provide a one-piece dental floss apparatus which is placed on only one finger or thumb, thus requiring insertion of only the finger or thumb into the mouth for flossing.

Further objects and advantages of the invention will be brought out in the following portions of the specification, wherein the detailed description is for the purpose of fully disclosing preferred embodiments of the invention without placing limitations thereon.

BRIEF DESCRIPTION OF THE DRAWINGS

The invention will be more fully understood by reference to the following drawings which are for illustrative purposes only.

DETAILED DESCRIPTION OF THE INVENTION

Referring more specifically to the drawings, for illustrative purposes the present invention is embodied in the apparatus generally shown in FIG. 1 through FIG. 18, wherein like reference numerals denote like parts. It will be appreciated that the apparatus may vary as to configuration and as to details of the parts without departing from the basic concepts as disclosed herein.

Figure 1:
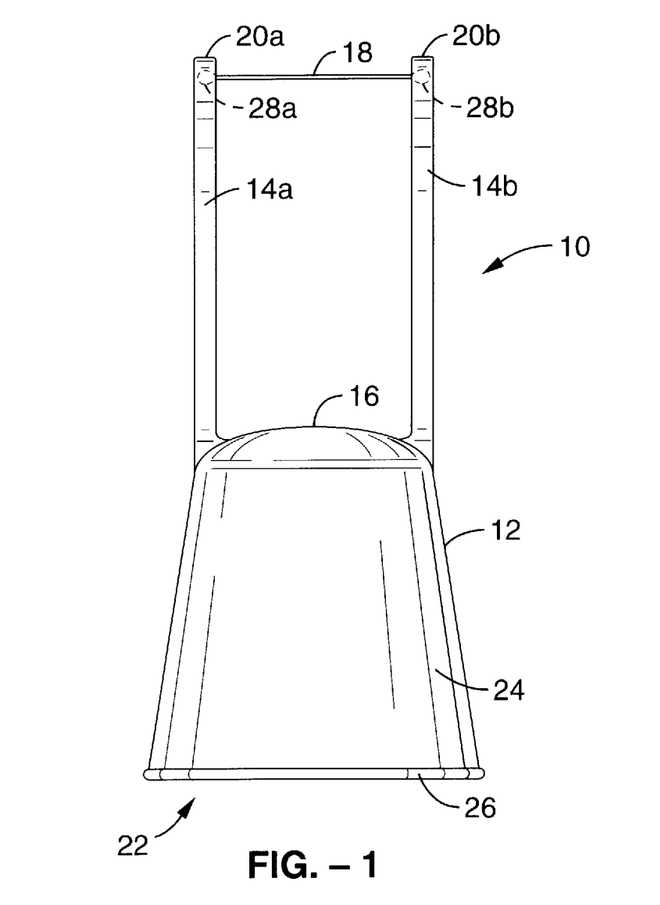
FIG. 1 is a front view of a dental flossing apparatus in accordance with the present invention.
Figure 2:
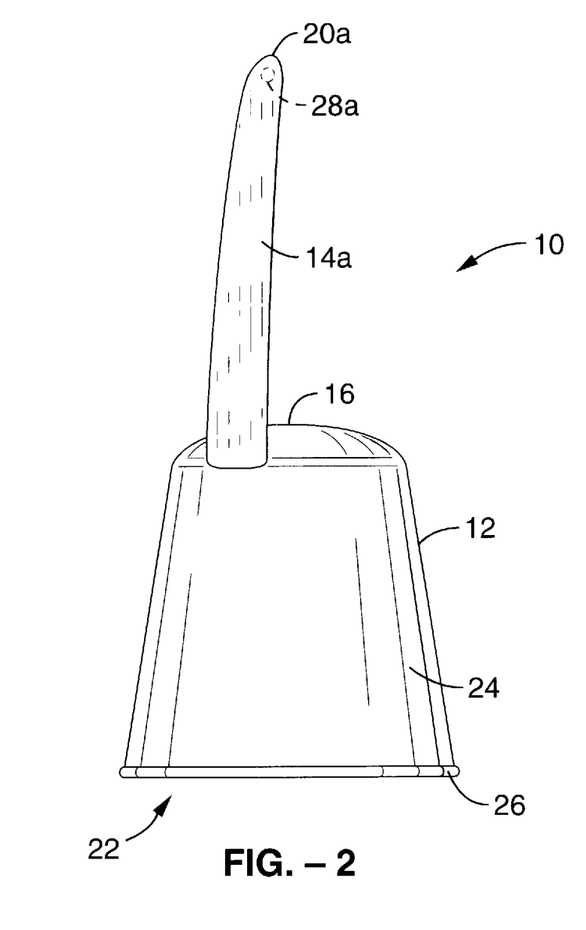
FIG. 2 is a side view of the dental flossing apparatus shown in FIG. 1.

Referring to FIG. 1 and FIG. 2, a finger flossing apparatus 10 in accordance with the present invention is generally shown. Apparatus 10 generally comprises a thimble 12, a pair of tines 14a, 14b extending from the distal end 16 of thimble 12, and a section of dental floss 18 is horizontally suspended between the tips 20a, 20b of tines 14a, 14b, respectively. Tines 14a, 14b can be configured to either be straight, or curved as shown in FIG. 2, and are typically about ¾ inches long.

Thimble 12 has an opening 22 sized and configured to receive the tip of a finger or thumb therein. The wall 24 of thimble 12 is preferably distally tapered to generally match a fingertip's profile, and distal end 16 of thimble is generally convex. Thimble 12 can be sized to accommodate all the varying finger sizes from children to adults, and thimble 12 is preferably fabricated from an elastic material, such as rubber, ABS plastic or polypropylene, to better conform to the fingertip of the user and to provide a better grip when worn. Where a collapsible elastic material is used, a band 26 is provided around opening 22 to hold open and facilitate placement of apparatus 10 over the tip of the finger or thumb, much like a finger cot.

Dental floss 18 is preferably fabricated from puffed Teflon™ or other similarly tough floss material. However, those skilled in the art will appreciate that use of apparatus 10 can be practiced with any type of dental floss. Dental floss 18 is permanently affixed at points 28a, 28b adjacent tips 20a, 20b of tines 14a, 14b during manufacturing by an injection molding process that also forms thimble 12 and tines 14a, 14b of apparatus 10. In this embodiment, tines 14a, 14b can either be rigid or semi-rigid. Apparatus 10 manufactured in this manner is a single-use disposable article.

To use apparatus 10 for flossing teeth, thimble 12 is inserted over the tip of any finger or thumb. Since some manipulation of the finger or thumb within the mouth is necessary during flossing with apparatus 10, the preferred finger used for flossing with apparatus 10 is the index finger, as most users have better control of their index fingers. Thimble 12 is sized such that a fairly tight fit results with the finger is inserted therein, and the elasticity of thimble 12 serve to better grip thimble around the tip of the finger. A vacuum is also created after insertion of the finger into thimble 12, which further aids in securely holding thimble 12 onto the finger or thumb. Once thimble 12 is in place over the finger or thumb tips, apparatus 10 is maneuvered within the mouth so that dental floss 18 can be slid between teeth for flossing action.

Figure 3:
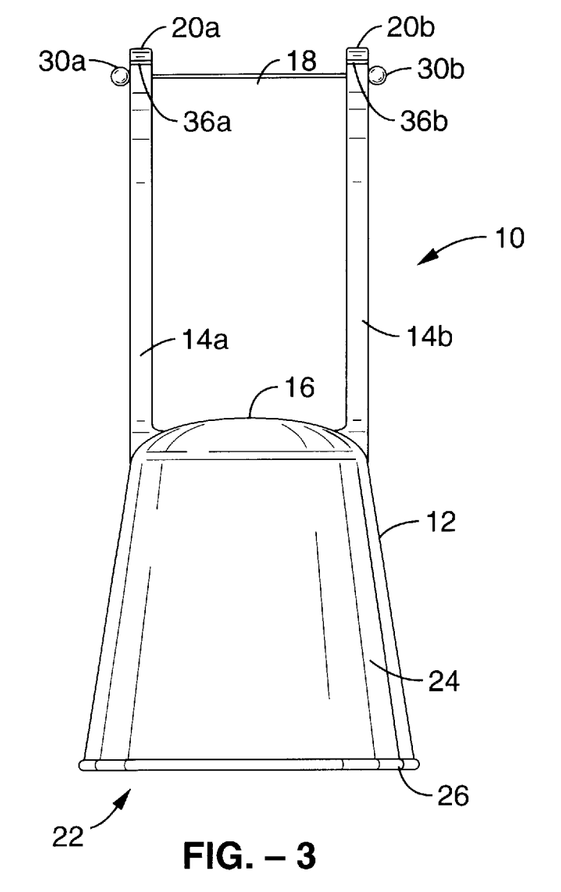
FIG. 3 is a front view of an alternative embodiment of a dental flossing apparatus in accordance with the present invention.
Figure 4:
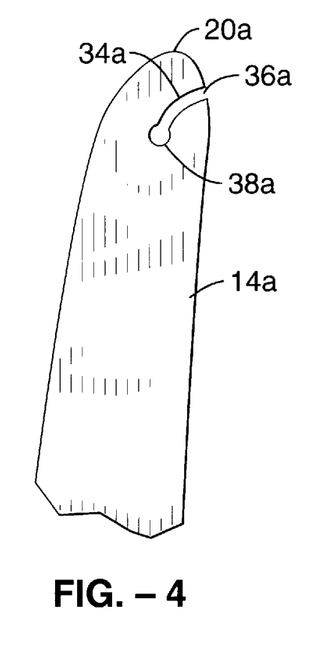
FIG. 4 is a fragmentary detail view of the tine portion of the apparatus shown in FIG. 3.
Figure 5:
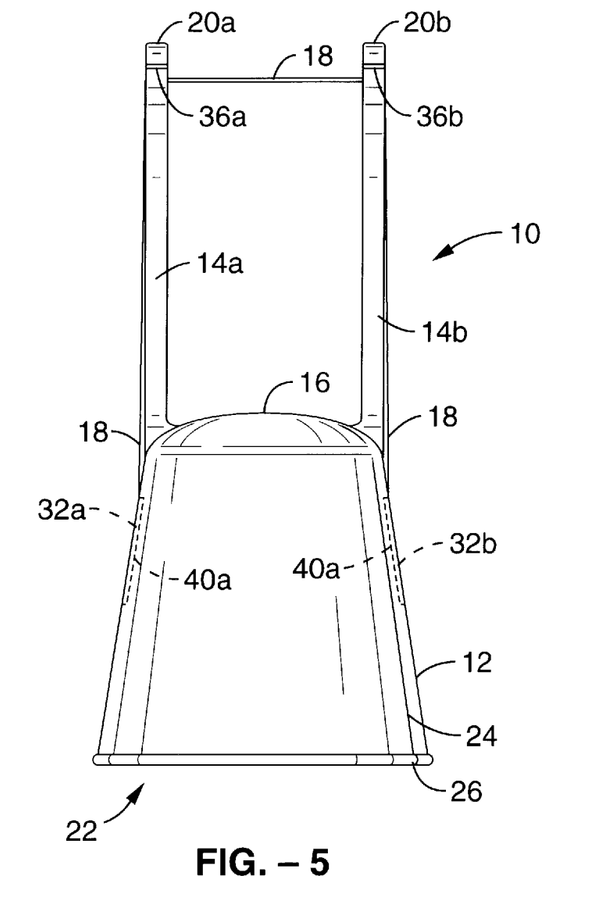
FIG. 5 is a front view of a second alternative embodiment of a dental flossing apparatus in accordance with the present invention.
Figure 6:
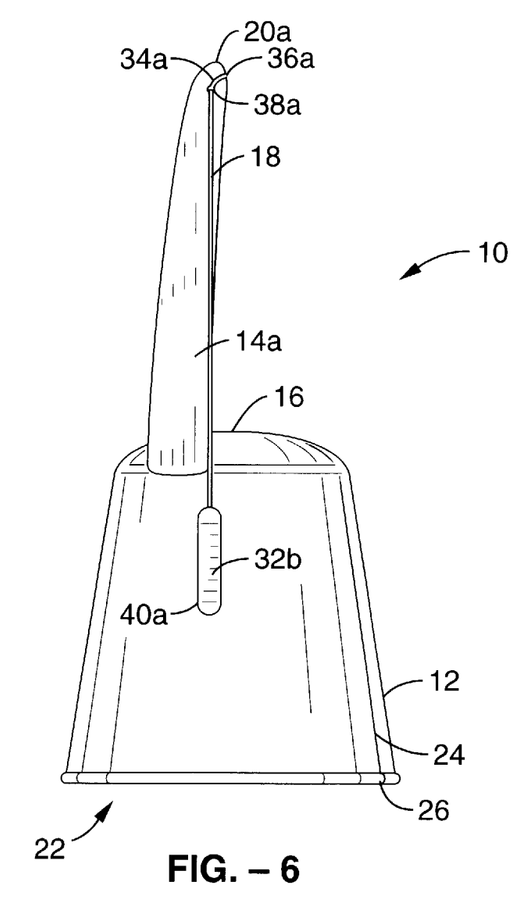
FIG. 6 is a fragmentary detail view of the tine portion of the apparatus shown in FIG. 5.

Various other means for supporting dental floss 18 on thimble 12 are also contemplated. These alternative attachment means provide for the removal and replacement of dental floss 18, thus rendering apparatus 10 reusable. For example, as shown in FIG. 3 through FIG. 6, an alternative embodiment and a second alternative embodiment of apparatus 10 is generally shown. Dental floss 18 can include gripper handles 30a, 30b as shown in FIG. 3 or gripper handles 32a, 32b, as shown in FIG. 5 and FIG. 6, which are disposed at each end of the dental floss as taught in U.S. Pat. No. 4,016,892, which is incorporated herein by reference. The gripper handles can be spherical as shown in FIG. 3, elongated as shown in FIG. 5 and FIG. 6, or any other shape (e.g., hex, triangular, star-shaped, etc.) that is desired and convenient for attachment and use.

To accommodate dental floss 18 having gripper handles, a channel or slot 34a, 34b is disposed adjacent each tip 20a, 20b of tines 14a, 14b. Each slot 34a, 34b preferably has an opening 36a, 36b for the insertion of dental floss 18 therein. Slots 34a, 34b and openings 36a, 36b are sized to receive and allow passage of dental floss 18 therethrough. To prevent dental floss 18 from slipping off during flossing, slots 34a, 34b preferably follow an arced or curvilinear path from openings 36a, 36b to receptacles 38a, 38b, respectively, which receive the gripper handles. In the embodiments shown, receptacles 38a, 38b are semi-spherical depressions to receive spherical gripper handles, but it will be appreciated that neither the shape of the gripper handles nor that of the receptacles is limited.

In the embodiment shown in FIG. 3, tines 14a, 14b are preferably sufficiently flexible that they can be flexed toward each other for attachment of dental floss 18, and dental floss 18 preferably has a length slightly less than the distance between tips 20a, 20b when tines 14a, 14b are in a relaxed position (no floss installed). Receptacles 38a, 38b are sized to be smaller than gripper handles 30a, 30b to prevent passage of gripper handles 30a, 30b therethrough. As dental floss 18 is placed in receptacles 38a, 38b, tines 14a, 14b are flexed toward each other. The tendency for tines 14a, 14b to return to their relaxed position serves to maintain constant tautness on dental floss 18 necessary for flossing.

In the second alternative embodiment shown in FIG. 5 and FIG. 6, gripper handles 32a, 32b are inserted into receptacles 40a, 40b, respectively, as shown. Receptacles 40a, 40b are disposed on wall 24 of thimble 12 below tines 14a, 14b, respectively. Receptacles 40a, 40b are sized to snugly receive gripper handles 32a, 32b therein and to securely maintain said handles in place during flossing. The length of dental floss 18, in conjunction with the position of receptacles 40a, 40a provides for tautness of dental floss 18 when placed on apparatus 10. It will be appreciated that the means for suspending dental floss between the tines shown in FIG. 3 and FIG. 4 and between the tine and the thimble shown in FIG. 5 and FIG. 6 could be combined. For example, a hybrid could be configured where one gripper handle is retained by the tip of a tine as in FIG. 3, while the other gripper handle fits into a receptacle in the thimble as shown in FIG. 6.

Figure 7:
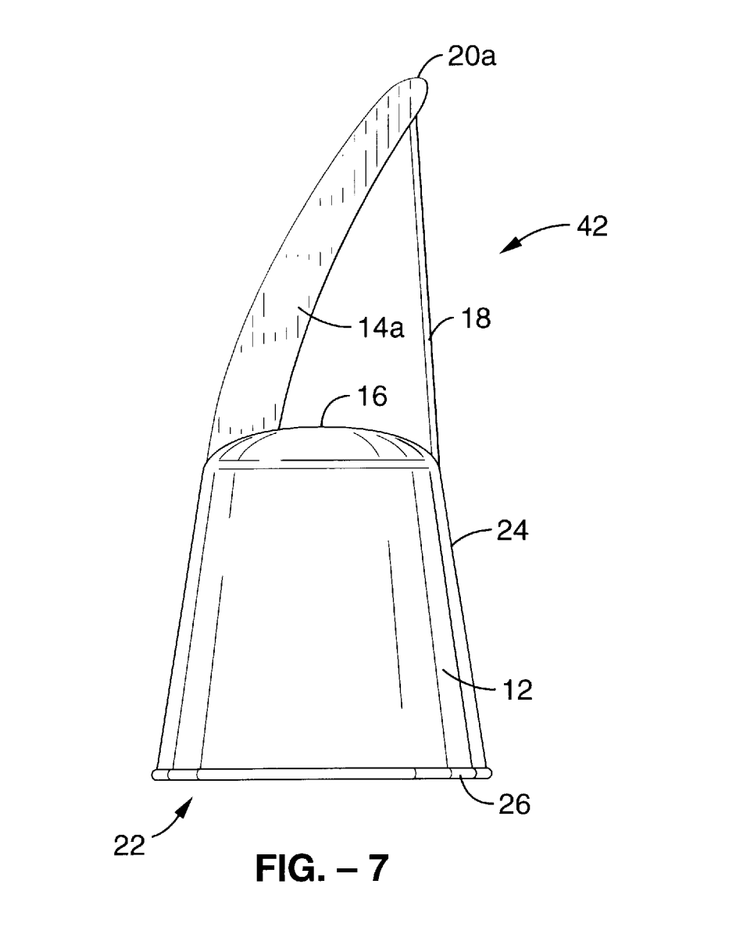
FIG. 7 is a side view of a third alternative embodiment of a dental flossing apparatus in accordance with the present invention.
Figure 8:
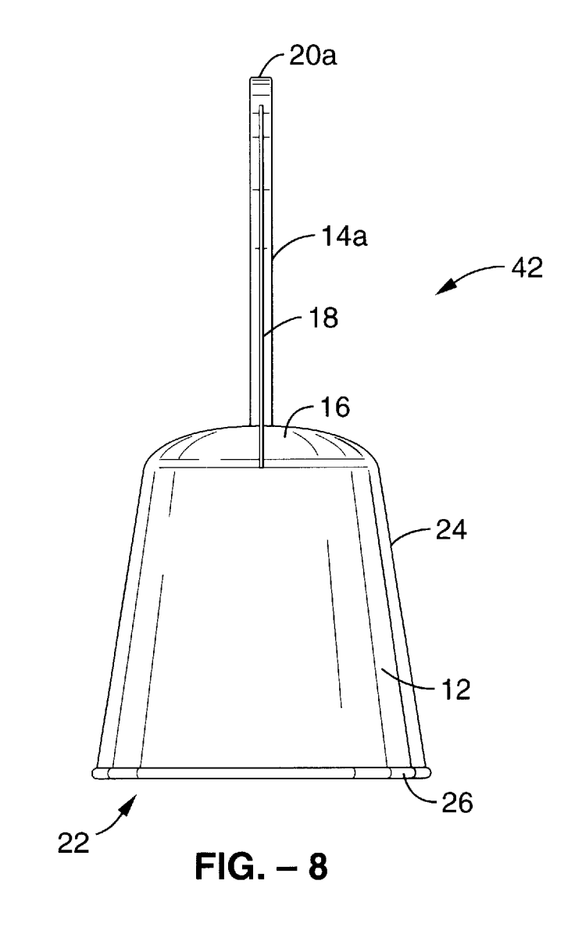
FIG. 8 is a front view of a the dental flossing apparatus shown in FIG. 7.

Referring also to FIG. 7 and FIG. 8, a third alternative embodiment 42 of the present invention is generally shown wherein still another means for supporting dental floss 18 from thimble can be seen. A single tine 14a extends from the distal end 16 of thimble 12 and dental floss 18 is suspended between tip 20a of tine 14a and thimble 12. Tine 14a is typically angled or curved, as shown in FIG. 7, to better allow for the vertical suspension of dental floss 18, and is preferably centered as shown in FIG. 8.

Dental floss 18 can be attached to either wall 24 or distal end 16 of thimble 12. Dental floss 18 is preferably fixedly attached to both tip 20a of tine 14a and thimble 12 during manufacture by an injection molding process. This embodiment is particularly well suited to flossing anterior teeth such as rear molars. It will also be appreciated that, as an alternative, dental floss with gripper handles could be used. Here, the tip of the tine would be configured similarly to that shown in the alternative embodiment of FIG. 3 and FIG. 4, and the receptacle in the thimble would be like that shown in second alternative embodiment of FIG. 6.

Figure 9:
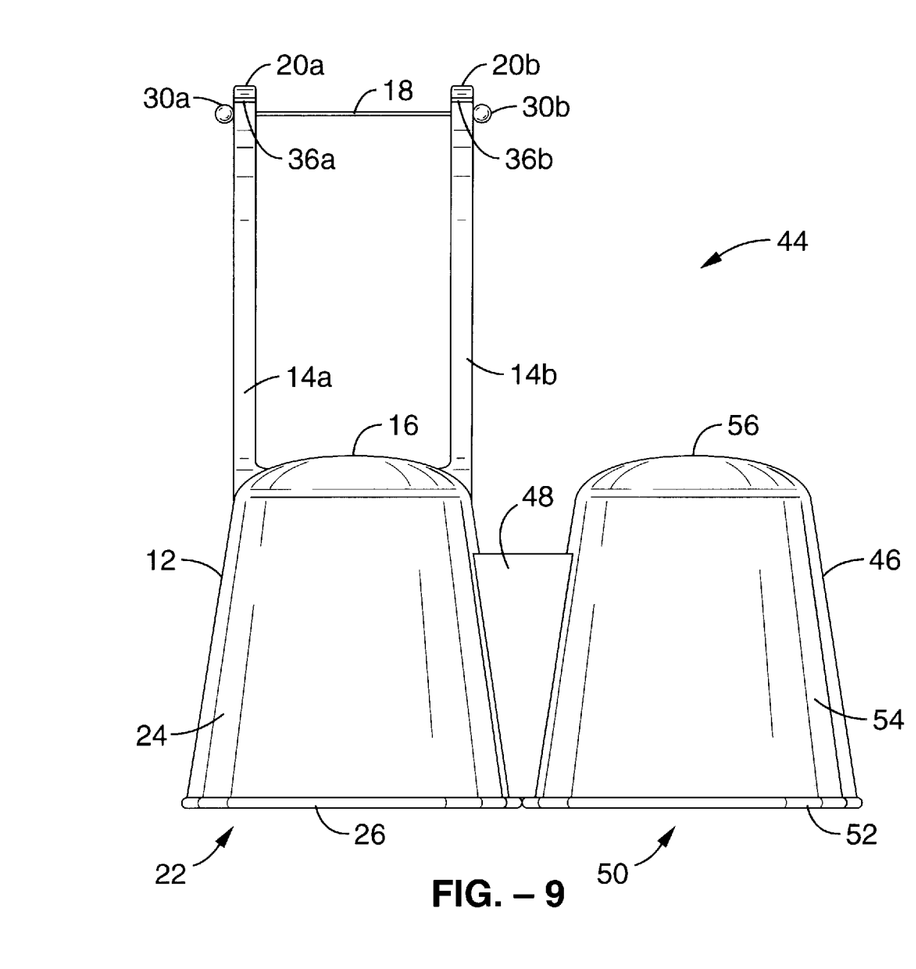
FIG. 9 is a front view of a fourth alternative embodiment of a dental flossing apparatus in accordance with the present invention.
Figure 10:
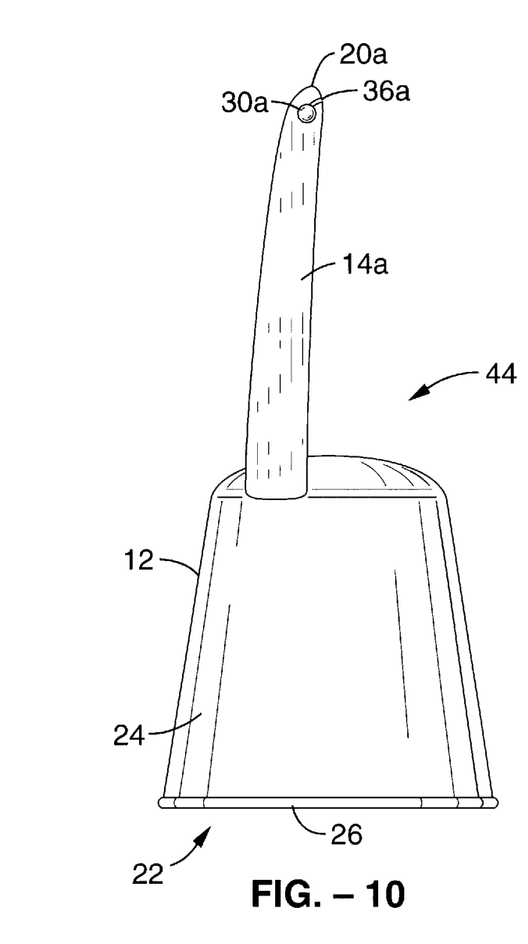
FIG. 10 is a side view of a dental flossing apparatus shown in FIG. 9.

Referring now to FIG. 9 and FIG. 10, a fourth alternative embodiment of a dental flossing apparatus is generally shown. Here, a second thimble 46 is used in conjunction with thimble 12 to allow for additional torque control and leverage during flossing. Second thimble 46 is placed in tandem with thimble 12 and connected thereto by a bridge 48. Second thimble includes an opening 50, a band 52 peripherally disposed around opening 50, a tapered wall 54 extending from opening 50 and a convex-shaped distal end 56. Bridge 48 is attached to wall 24 of thimble 12 and wall 54 of second thimble 46. Tines 14a, 14b is fixedly attached and extends from distal end 16 of thimble 12, as also shown in the first embodiment. It is also contemplated that tines 14a, 14b can extend from distal end 56 of second thimble 46. It is further contemplated that tine 14a may extend from thimble 12 while tine 14b may extend from second thimble 46. Tines 14a, 14b are formed with thimbles 12, 46 during manufacturing preferably by an injection molding process. The additional of second thimble 46 in tandem to thimble 12 permits two adjacent fingers to be used to floss which increases the user's torque control and leverage especially when flossing hard to reach areas within the mouth.

Figure 11:
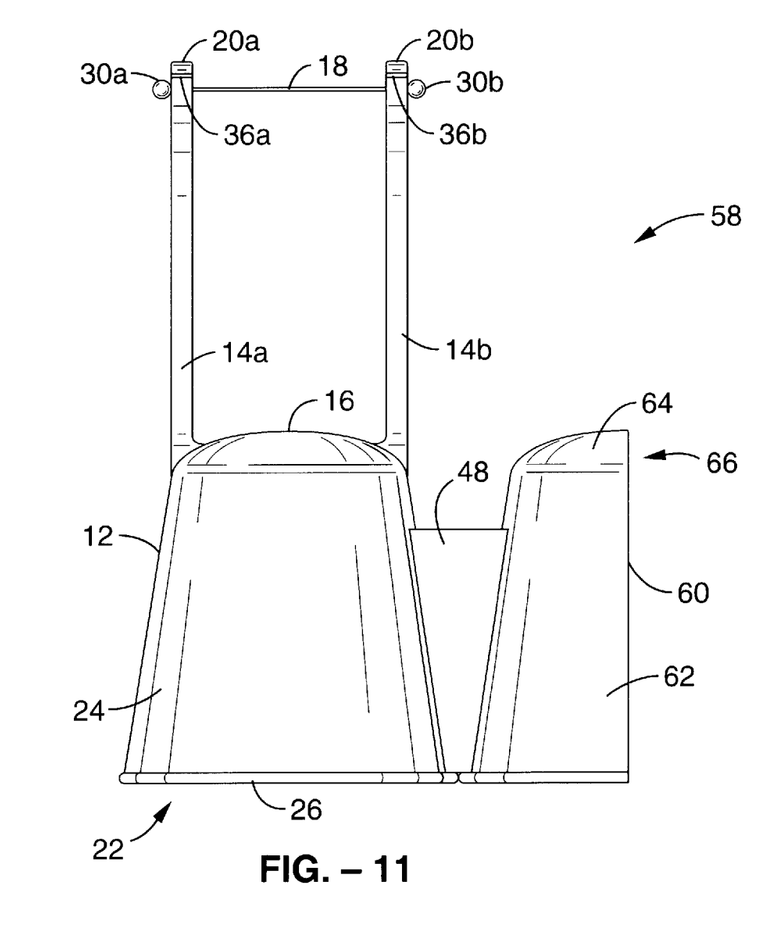
FIG. 11 is a front view of a fifth alternative embodiment of a dental flossing apparatus in accordance with the present invention.

Referring also to FIG. 11, a fifth alternative embodiment 58 of a dental flossing apparatus is generally shown. In this embodiment, a finger holder 60 is attached in tandem to thimble 12 by bridge 48. Finger holder 60 comprises a semi-circular member having a tapered wall 62 that extends to a cover 64 located adjacent its distal end 66 longitudinally separated approximately adjacent its midpoint. Cover 64 and wall 62 form a void (not shown) configured to receive and hold a finger therein. Finger holder 60 increases the user's torque control and leverage.

Figure 12:
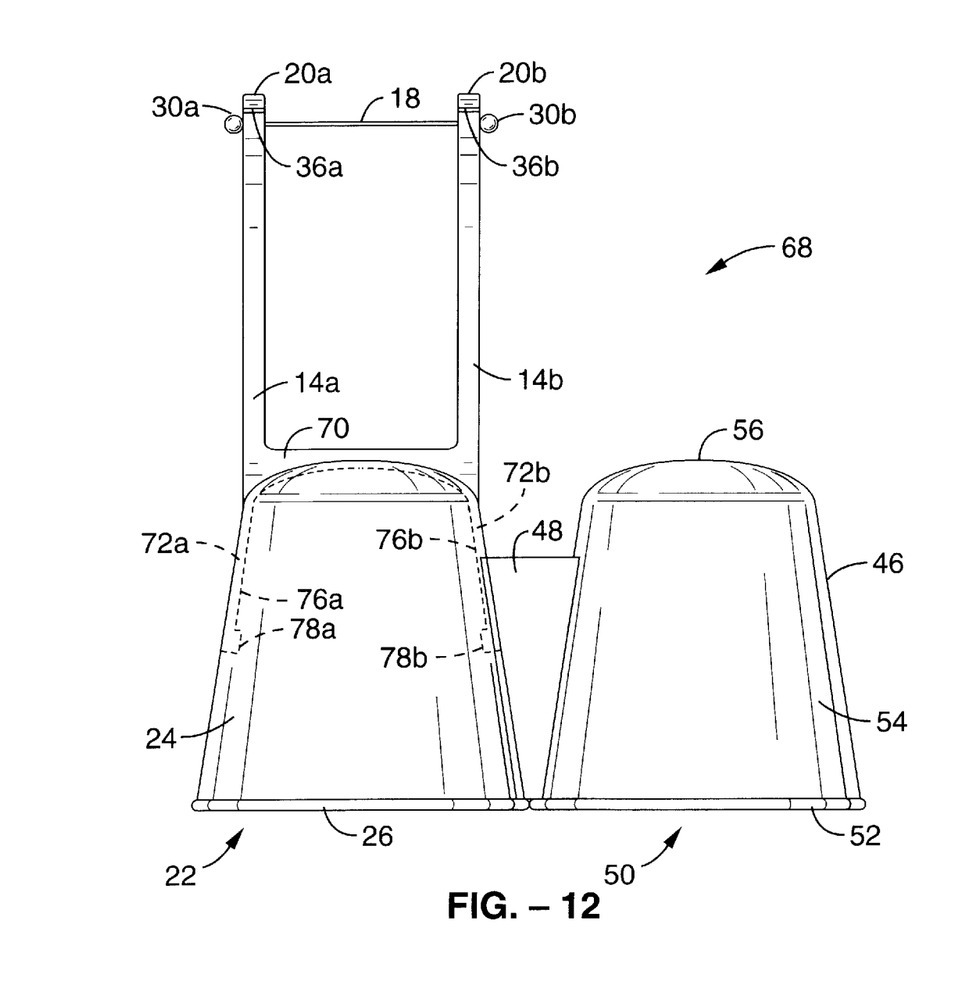
FIG. 12 is a front view of a sixth alternative embodiment of a dental flossing apparatus in accordance with the present invention.
Figure 13:
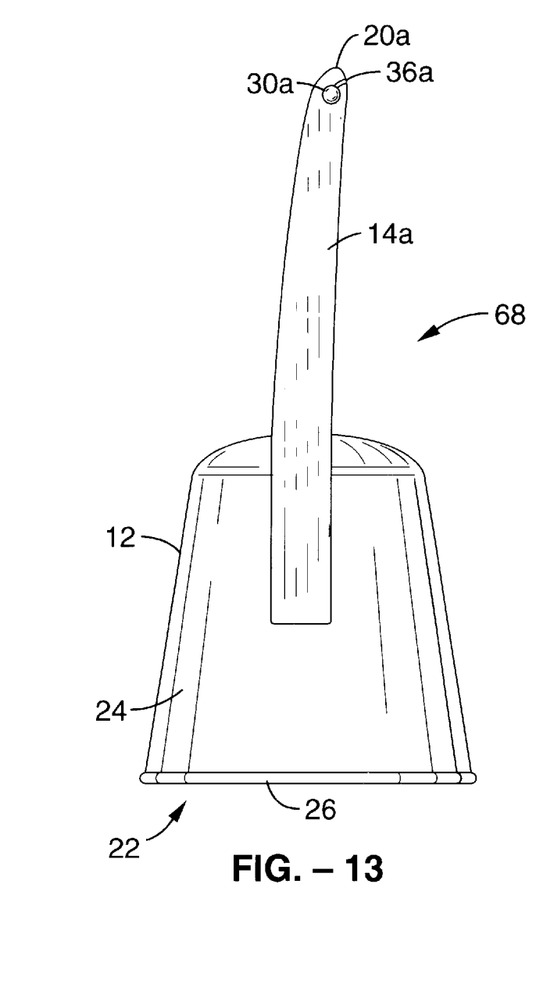
FIG. 13 is a side view of a dental flossing apparatus shown in FIG. 12.
Figure 14:
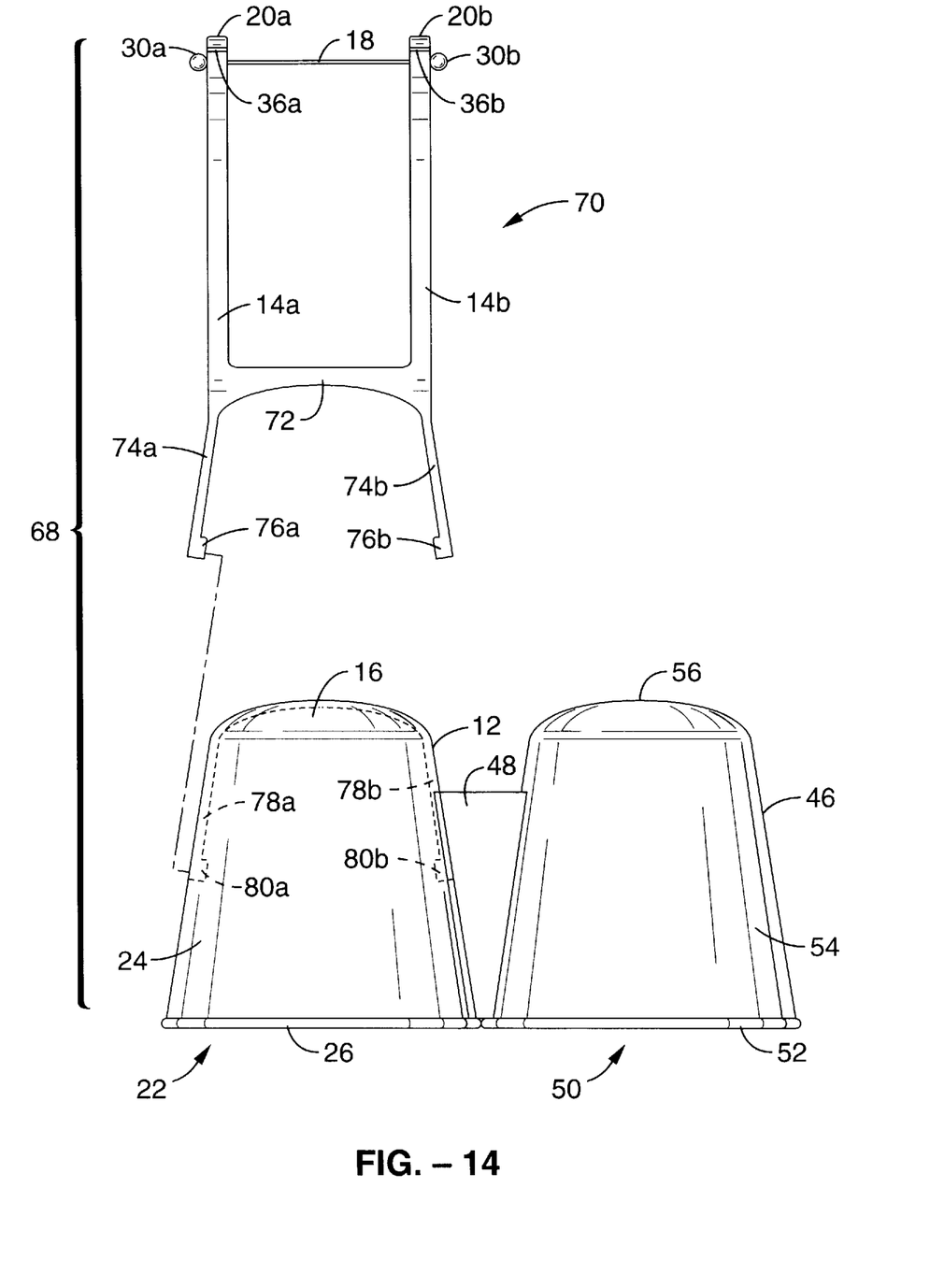
FIG. 14 is an exploded view of a dental flossing apparatus shown in FIG. 12.

In FIG. 12 through FIG. 14, a sixth alternative embodiment 68 of a dental flossing apparatus is generally shown.

Tines 14a, 14b are part of a tine assembly 70 that is detachable from thimble 12. Assembly 70 comprises a cross-member 72 connecting tines 14b, 14b together in a generally parallel fashion. A pair of legs 74a, 74b extend downwardly from cross-member 72. Legs 74a, 74b each includes a tang 76a, 76b, respectively, at their lower end, which is adapted to slidably engage within a pair of longitudinally-disposed grooves 78a, 78b along wall 42 of thimble 12. Grooves 78a, 78b are spaced approximately 180° apart and extend downward from distal end 16 of thimble 12 to approximately the mid-section of thimble 12. A pair of recesses 80a, 80b are located within grooves 78a, 78b, respectively to serve as anchor points for tangs 76a, 76b. Legs 74a, 74b are somewhat flexible and naturally spaced such that when tangs 76a, 76b are inserted into respective recesses 80a, 80b, legs 74a, 74b exert pressure on wall 24 of thimble 12 to help maintain tangs 76a, 76b within recesses 80a, 80b, during stresses encountered by dental floss 18 during flossing. It is contemplated that recesses 80a, 80b can be also located on wall 54 of second thimble 46, providing the user the option of which thimble to place tine assembly 70 upon.

Figure 15:
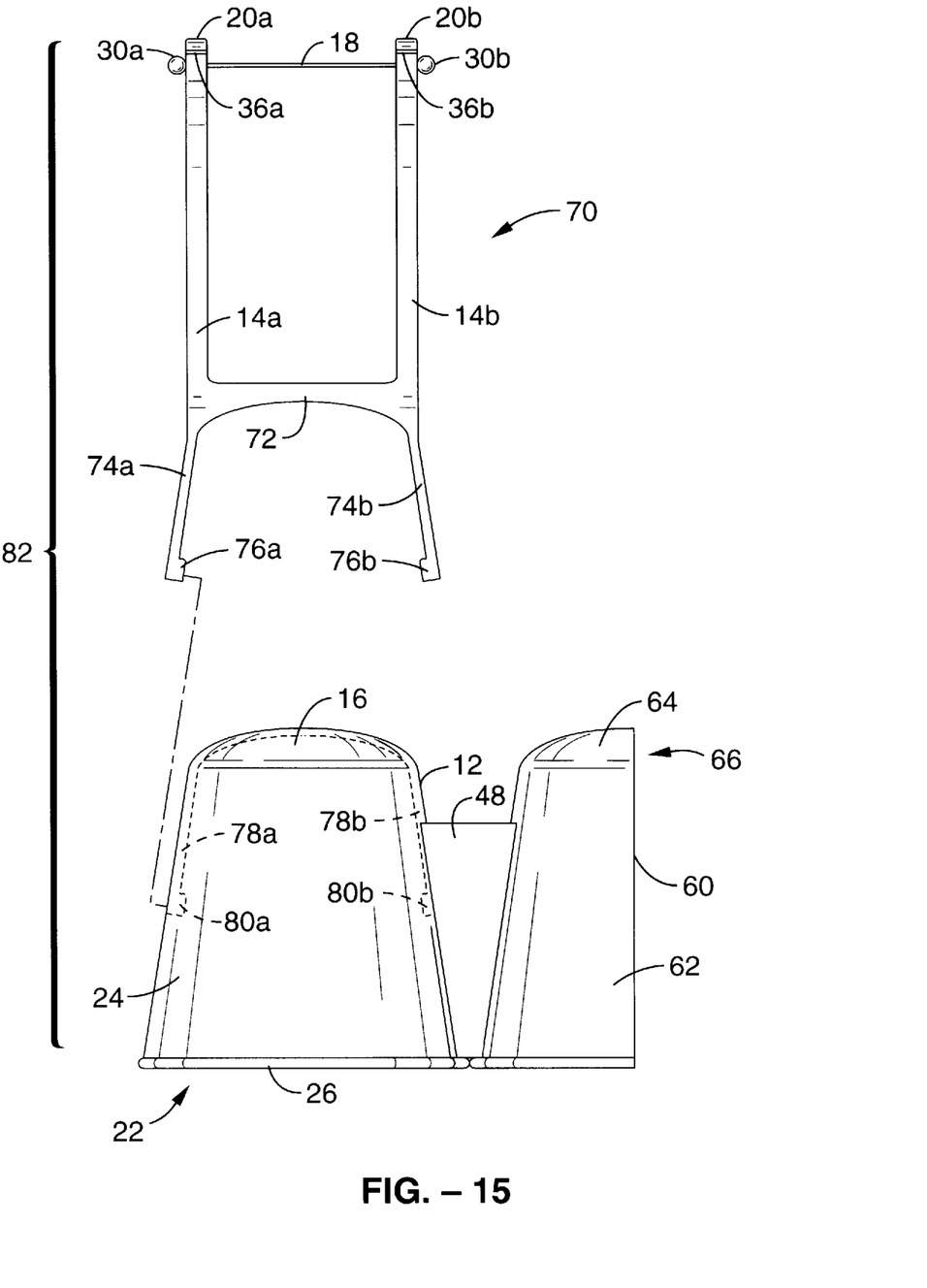
FIG. 15 is an exploded front view of a seventh alternative embodiment of a dental flossing apparatus in accordance with the present invention.

In FIG. 15, a seventh alternative embodiment 82 of a dental flossing apparatus is generally shown. Tine assembly 70 is adapted to attach onto thimble 12 which includes finger holder 60 tandemly attached thereto. The configuration and benefits provided by finger holder is discussed above with respect to fifth alternative embodiment 58.

Figure 16:
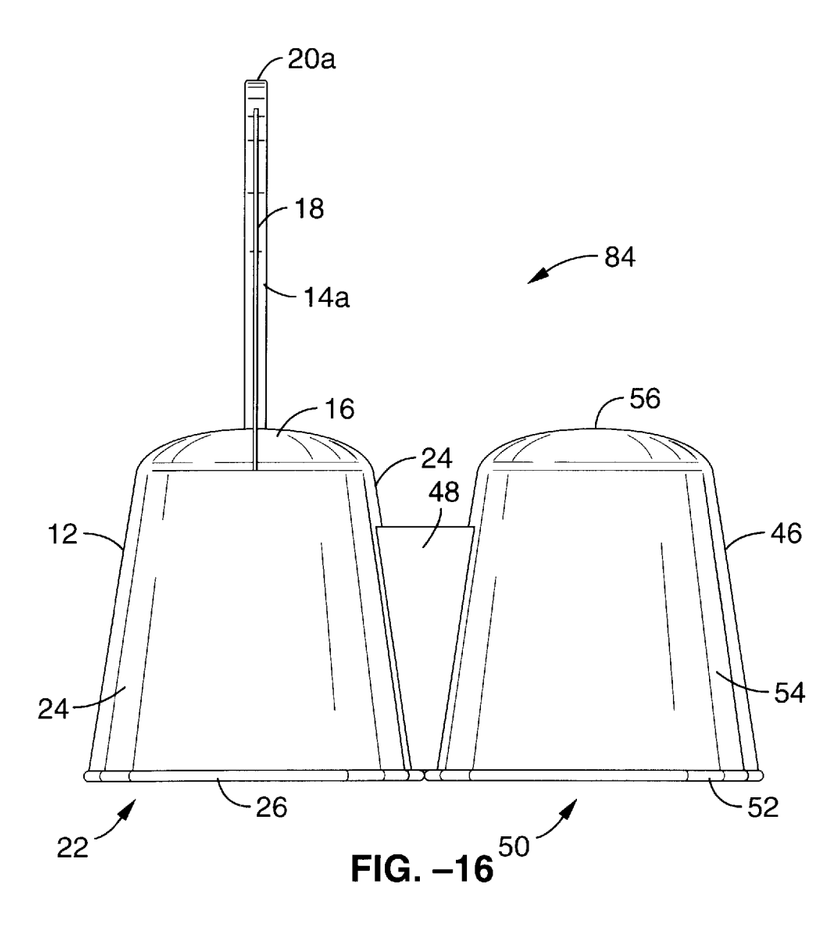
FIG. 16 is a front view of an eighth alternative embodiment of a dental flossing apparatus in accordance with the present invention.
Figure 17:
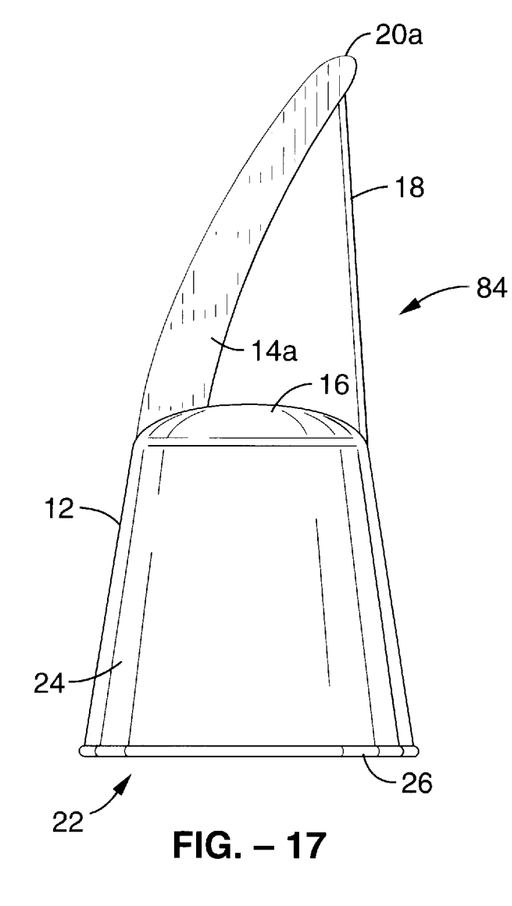
FIG. 17 is a side view of a dental flossing apparatus shown in FIG. 16.

Referring to FIG. 16 and FIG. 17, an eighth alternative embodiment 84 of a dental flossing apparatus is generally shown. Dental floss 18 is attached onto thimble 12 by single tine 14a, and second thimble 46 is tandemly attached to thimble 12 by bridge 48.

Figure 18:
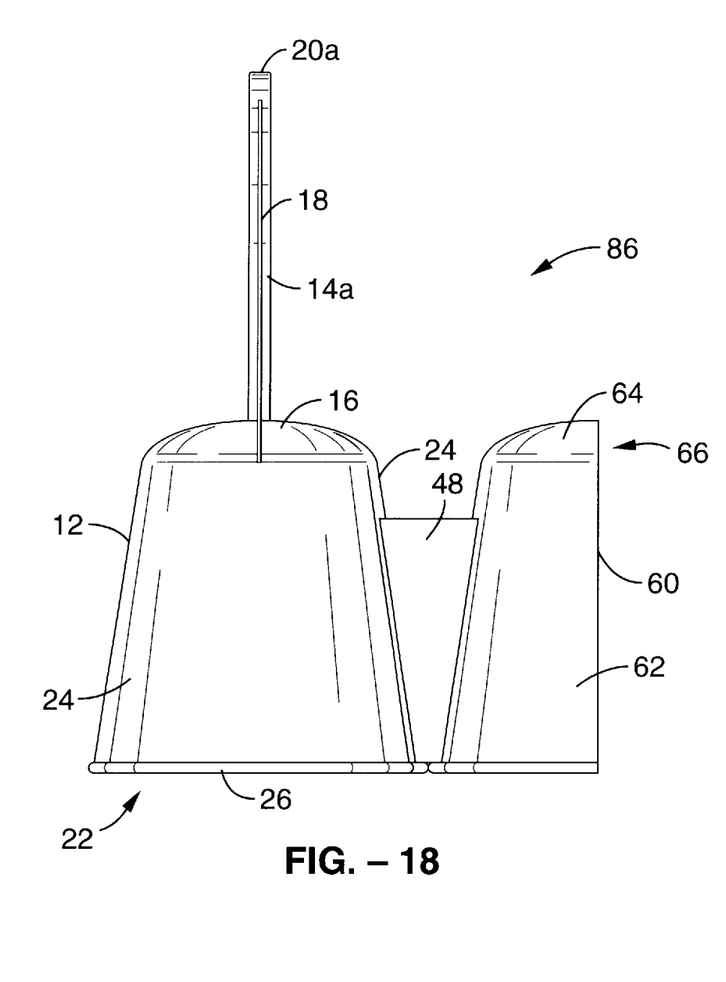
FIG. 18 is a front view of a ninth alternative embodiment of a dental flossing apparatus in accordance with the present invention.

In FIG. 18, a ninth alternative embodiment 86 of a dental flossing apparatus is generally shown. In addition to dental floss 18 attached to thimble 12 by single tine 14a, finger holder 60 is tandemly attached to thimble 12.

Accordingly, it will be seen that this invention eliminates the problems commonly associated with flossing teeth by using a teeth flossing apparatus that is placed over the tip of a finger or thumb. Although the description above contains many specificities, these should not be construed as limiting the scope of the invention but as merely providing illustrations of some of the presently preferred embodiments of this invention. Thus the scope of this invention should be determined by the appended claims and their legal equivalents.

What is claimed is:

1. An apparatus for flossing teeth, comprising:
  (a) a first thimble; and
  (b) a pair of spaced-apart tines extending from said first thimble.

2. An apparatus as recited in claim 1, further comprising dental floss extending between said pair of spaced-apart tines.

3. An apparatus as recited in claim 1, further comprising a second thimble attached in tandem to said first thimble.

4. An apparatus as recited in claim 1, wherein said pair of spaced-apart tines are detachable from said first thimble.

5. An apparatus as recited in claim 1, further comprising a finger holder attached in tandem to said first thimble.

6. An apparatus for flossing teeth, comprising:
  (a) a first thimble; and
  (b) a pair of tines extending from said first thimble, each said tine including a tip.

7. An apparatus as recited in claim 6, further comprising dental floss extending between the tips of said tines.

8. An apparatus as recited in claim 6, further comprising means for suspending dental floss between said tips of said tines.

9. An apparatus as recited in claim 6, further comprising a second thimble attached in tandem to said first thimble.

10. An apparatus as recited in claim 9, further comprising dental floss extending between the tips of said tines.

11. An apparatus as recited in claim 9, further comprising means for suspending dental floss between said tips of said tines.

12. An apparatus as recited in claim 9, wherein said pair of tines are detachable from said thimble.

13. An apparatus as recited in claim 6, further comprising a finger holder attached in tandem to said first thimble.

14. An apparatus as recited in claim 13, further comprising dental floss extending between the tips of said tines.

15. An apparatus as recited in claim 13, further comprising means for suspending dental floss between said tips of said tines.

16. An apparatus as recited in claim 13, wherein said pair of tines are detachable from said thimble.

17. An apparatus for flossing teeth, comprising:
    (a) a thimble;
    (b) an arcuate tine extending from said thimble; and
    (c) dental floss extending between said tine and said thimble.

18. An apparatus as recited in claim 17, further comprising a second thimble attached in tandem to said first thimble.

19. An apparatus as recited in claim 17, further comprising a finger holder attached in tandem to said first thimble.

20. An apparatus for flossing teeth, comprising:
    (a) a first thimble;
    (b) a second thimble attached in tandem to said first thimble; and
    (c) means for supporting dental floss from said first thimble.

21. An apparatus as recited in claim 20, wherein said means for supporting dental floss from said first thimble comprises a tine extending from said first thimble.

22. An apparatus as recited in claim 21, further comprising dental floss extending between said tine and said first thimble.

23. An apparatus as recited in claim 20, wherein said means for supporting dental floss from said first thimble comprises a pair of spaced-apart tines extending from said first thimble.

24. An apparatus as recited in claim 23, wherein said pair of spaced-apart tines are detachable from said first thimble.

25. An apparatus as recited in claim 23, further comprising dental floss extending between said spaced-apart tines.

26. An apparatus for flossing teeth, comprising:
    (a) a first thimble;
    (b) a finger holder attached in tandem to said first thimble; and
    (c) means for supporting dental floss from said first thimble.

27. An apparatus as recited in claim 26, wherein said means for supporting dental floss from said first thimble comprises a tine extending from said first thimble.

28. An apparatus as recited in claim 27, further comprising dental floss extending between said tine and said first thimble.

29. An apparatus as recited in claim 26, wherein said means for supporting dental floss from said first thimble comprises a pair of spaced-apart tines extending from said first thimble.

30. An apparatus as recited in claim 29, wherein said pair of spaced-apart tines are detachable from said first thimble.

31. An apparatus as recited in claim 26, further comprising dental floss extending between said spaced-apart tines.

* * * * *